United States Patent [19]

Effenberger et al.

[11] Patent Number: 5,025,002
[45] Date of Patent: Jun. 18, 1991

[54] PROCESS FOR CONTROL OF MICROORGANISMS WITH PHOSPHORUS-BASED COMPOSITIONS

[75] Inventors: Reinhard Effenberger, Haifa; David Direktor, Qiryat Ata, both of Israel

[73] Assignee: Bromine Compounds Ltd., Beer-Sheva, Israel

[21] Appl. No.: 238,722

[22] Filed: Aug. 31, 1988

[51] Int. Cl.$^5$ ............................................. A01N 57/00
[52] U.S. Cl. ................................. 514/112; 514/119; 514/120
[58] Field of Search ........................................ 514/112

[56] References Cited

U.S. PATENT DOCUMENTS

| | | | |
|---|---|---|---|
| 2,995,486 | 8/1961 | Sallmann | 167/22 |
| 3,764,676 | 10/1973 | Kerst et al. | 514/112 |
| 4,285,765 | 8/1981 | Pera et al. | 162/161 |

OTHER PUBLICATIONS

Patent Abstract 96:176146y, Fr. Demande FR 2,484,392 (Cl. C02F1/50), Dec. 18, 1981, p. 257.
Charlot et al., Quantitative Inorganic Analysis, 1957, p. 385.
Process Biochemistry, Jul./Aug. 1976, p. 31.

Primary Examiner—Allen J. Robinson
Attorney, Agent, or Firm—Foley & Lardner

[57] ABSTRACT

Phosphorus-based compositions useful as biocides for the control of a broad spectrum of harmful micoorganisms are disclosed. The compositions contain at least one compound of the general formula $$(RO)_2P(O)CXYZ$$

wherein R is H, a $C_{1-12}$ aliphatic hydrocarbon radical or a phenyl radical, X is H or halogen, Y is halogen, and Z is a substitutent selected from the group consisting of COOH, CN, COOR and $CONR_2$, with the proviso that X and Y cannot both be Cl. The effective concentrations of the biocides vary according to the specific system, generally being in the range of between 0.1 to 5000 parts per million of substrate. The compositions may be employed alone or in the form of mixtures with other known compatible active agents. The compositions show high biocidal activity against various microorganisms in comparison with known biocides.

8 Claims, No Drawings

PROCESS FOR CONTROL OF MICROORGANISMS WITH PHOSPHORUS-BASED COMPOSITIONS

BACKGROUND OF THE INVENTION

The present invention relates to compositions useful as biocides for the control of harmful microorganisms. More particularly the invention relates to phosphorus-based compositions possessing outstanding biocidical properties for a wide spectrum of applications.

As known, a phenomenon which occurs in industrial process systems and products as well as in natural materials and their processing is the development of contamination by microorganisms if means are not taken to inhibit their growth. Wood pulp, wood chips, starch and proteinaceous substances, animal hides, vegetable tanning liquors and leather and damaged or degraded by bacteria and other microorganisms or by enzymes produced by their growth.

Plants, in growth and in storage, as well as plant products are subject to microbiological contamination. Wet pulp containing about 25% moisture content is subject to attack by stain, mold, and decay fungi. If not controlled, the result is a loss of useful fiber in badly decayed pulp, difficulty in dispersing partially decayed pulp, a darkening in colour and the development of undesirable odors caused by the growth of the microorganisms. Different species of molds are encountered at various stages in the manufacture of leather. As an example, soaking provides an environment highly conducive to the growth of microorganisms, and even strongly pickled solutions are subject to attack by some microorganisms. Molds in particular may be troublesome and cause discoloration of the pickled stock, especially if it is held for a period of time. During the chrome tanning process, the chrome tanned stock held "in the blue" readily molds and is discoloured. Mold growth may also develop on heavy vegetable tanned leather during the drying period and produces spots and stains on either the flesh or grains sides. Other fields where the problem exists are petroleum drilling operations, metal working fluids and in the paint industry. Paint latexes can be destroyed and paint films deteriorate as a result of the attack of harmful microorganisms. Cooling towers can be adversely affected by biocontamination.

Another objectionable occurance in industrial process systems involving water is slime formation. Slime consists of matted deposits of microorganisms, fibers, and debris, and it may have a disagreable odor. The microorganisms involved in its formation are primarily various species of spore-forming and non-spore forming bacteria, particularly capsulated forms of bacteria which secrete gelatinous substances that envelop or encase the cells. Slime microorganisms also include filamentous bacteria, filamentous fungi of the mold type, yeast and yeast-like organisms.

Besides being objectionable from the standpoint of general cleanliness and sanitation in breweries, wineries, dairies, paper mills or other industrial plants or establishments, slime may interfere and produce plugging of screens in pulp and paper systems, thus reducing their efficiency. When large amounts of slime become incorporated in the paper sheet, its strength is reduced, and it may consequently break and require rethreading of the machine. In the paper itself, slime may be responsible for unsightly spots, holes and odors and may produce general discoloration throughout the sheet.

A large number of prior patents claim various compounds as biocides for the control of harmful organisms. Thus according to U.K. Patent Application No. 2,077,713, a mixture of iodoacetamides with amines or quaternary ammonium compounds is claimed for the control of microorganisms in swimming pools, ponds, cooling water, systems involving cellulosic compositions and starch pastes. U.S. Pat. No. 4,285,765 claims a synergistic microbiocidal composition comprising 2-(thiocyanomethylthio)-benzothiazole and 2,2-dibromo-3-nitrilopionamide. Preparations containing phosphorus and halogen-containing condensation products useful as insecticides are claimed in the U.S. Pat. No. 2,995,486. However, reagents which are effective as insecticides are often not effective against the broad spectrum of microorganisms encountered in the various industrial applications.

SUMMARY OF THE INVENTION

It is an object of the present invention to provide biocidal compositions possessing outstanding properties for the control of a broad spectrum of microorganisms that are responsible for the contamination of industrual process systems and the deterioration of natural and industrial products. It is another object of the present invention to provide a process for controlling the growth of slime-forming and other harmful microorganisms in aqueous systems such as petroleum industry, petroleum products, oil drilling operations, metal working fluids, wood preservation, pulp and paper mills systems, cooling water systems. Thus the invention consists in a process for the control of harmful microorganisms being characterized by the use of an effective amount of a preparation which contains as active ingredient at least one compound included in the general formula:

$$(RO)_2P(O)CXYZ$$

wherein R is H or an aliphatic, aromatic or alkylaromatic hydrocarbon radical having 1 to 12 carbon atoms, X is hydrogen or halogen, Y is halogen, and Z is a substitutent selected from the group consisting of COOH, CN, COOR and CONR$_2$, with the proviso that X and Y cannot both be Cl. The compound to be added will vary according to the specific system in which the preparations are used. Effective concentrations of these biocides range from 0.1 to 5000 parts per million parts of substrate. It should be understood, of course, that larger quantities of the compounds may be used with no detrimental effect, but such larger quantities will increase the cost of treatment with limited material benefit.

Among the various compounds included in the above general formula the following may be mentioned:

| Carboxylate | Amides |
|---|---|
| $(CH_3O)_2P(O)CHBrCOOC_2H_5$ | $(HO)_2P(O)CHBrCONHC_6H_{11}$ |
| $(CH_3O)_2P(O)CBr_2COOC_2H_5$ | $(C_2H_5O)_2P(O)CBr_2CONHC_6H_{11}$ |
| $(CH_3O)_2P(O)CCl_2COOC_2H_5$ | $(C_4H_9O)_2P(O)CHClCONHCH_3$ |
| $(—OC_2H_4O)P(O)CBr_2COOC_2H_5$ | |

| -continued | |
|---|---|
| $(C_2H_5O)_2P(O)CHClCOOCH_3$ | $(CH_3O)_2P(O)CBr_2CONH_2$ |
| $(C_6H_5O)_2P(O)CHBrCOOC_{12}H_{25}$ | $(C_2H_5O)(HO)P(O)CHClCONHC_4H_9$ |
| $(C_4H_9O)_2P(O)CBr_2COOC_6H_{4Br}$ | |
| Nitriles. | Carboxylic acids. |
| $(CH_3O)_2P(O)CHBrCN$ | $(HO)_2P(O)CHBrCOOH$ |
| $(CH_3O)_2P(O)CBr_2CN$ | $(HO)_2P(O)CHClCOOH$ |
| $(C_6H_5O)_2P(O)CHClCN$ | $(CH_3O)(HO)P(O)CHBrCOOH$ |
| $(C_{12}H_{25}O)_2P(O)CHBrCN$ | |

The use of the industrial biocides, encompassed by the general formula according to the present invention, may be divided into two basic categories:

1. Biocides added or used as an adjunct to an industrial process to ensure the efficient, safe, and economical operation of that process. Products or processes in this category include metal working fluids: latexes, resins, and other polymer emulsions used as intermediates; pigment slurries; clays and other mineral-type slurries; lignosulfonates; textile lubricants, spin finishes, anti-statics; cooling-tower waters; pulp and paper mill process waters and suspensions; secondary oil recovery systems; casein solution; gum solutions and other printing solutions, and silicone emulsions.

2. Biocides incorporated by a manufacturer into a finished product or into components of a finished product to prevent deterioration of disfigurement of the product. This category include wood, wood veneers, textile and textile products, waxes, leather hides, linseed-based paints, paper and paper board, plastic sheeting and plastics, optics, hoses and cords, rubber products, cement, water-based paints, inks, adhesives, glues etc.

As known in the art, in protecting aqueous products, the biocide must be sufficiently soluble to enter and remain in the water phase at a lethal concentration.

The biocidal compositions according to the present invention, have the advantages of being effective against a broad spectrum of microorganisms, are long lasting, stable and safe. They can be utilized, if desired, in the form of conventional formulations or compositions with diluents or extenders, i.e. dispersible carriers vehicles, such as solutions, suspensions emulsions, emulsifiable concentrates, spray powders, pastes, soluble powders, dusting agents, granulates etc. These are prepared in a known manner, for instance by extending the active compound with dispersible liquid diluent, carriers and/or dispersible solid carriers optionally with the use of carrier vehicle assistants, e.g. surface active agents, including emulsifying agents and/or dispersing agents. In the case where water is used as carrier vehicle, organic liquids may be added as auxiliary solvents. The following may be considered for use as carrier vehicle assistants, e.g. surface-active agents, for this purpose: emulsifying agents, such as nonionic and anionic emulsifying agents, (e.g. polyethylene oxide esters of fatty acids, polyethylene oxide ethers of fatty acids alcohols, alkyl sulfonates etc.) and dispersing agents such as lignin, sulfite waste liquors, methyl cellulose etc.

Such active compounds may be employed alone or in the form of mixtures with another and/or with other known, compatible active agents, such as other biocides and/or potentiating compounds such as EDTA (ethylene diamine tetraacetic acid), if desired, or in the form of particular dosage preparations for specific applications made therefrom, such as solutions, emulsions, suspensions, powders, pastes, granulates and aerosols which are thus ready for use.

Although the preferred use of the compositions according to the present invention is for the control of harmful microorganisms in aqueous industrial system process streams, they can also be successfully utilized in standing and running waters such as swimming pools and ponds and cooling water circuits. Especially in the latter case, conventional auxiliaries can additionally be employed in the use according to the present invention, for example corrosion inhibitors, anti-furring agents, water softeners, masking agents for example, phosphates, amides of phosphoric acid, phosphonic acids, polymeric carboxylic acids derived for example from acrylic acid or maleic acid, their anhydrides or salts, and their additives.

One of the advantages of the present invention, is that the chemical reagents present in the compositions claimed as biocides, can be easily prepared from commercially available raw materials. Some of the preferred compounds found in particular useful as biocides will be hereafter described, although it should be clearly understood that other compounds included in the formula given above may be prepared in a similar manner, their biodidal activity being very effective compared with other known biocides sold on the market.

EXAMPLE 1

Step (a): Preparation of ethyl(dimethylphosphono)acetate

An amount of 340.8 g of ethyl chloroacetate was mixed with 496 g of trimethyl phosphite in a reactor fitted with a thermometer, nitrogen inlet and a fractionation column (containing 5 mm Raschig rings as packing) topped with a variable reflux condenser. The reactor was heated to enable slow reflux in the column only followed by a slow increase in the temperature from 110 to 150 degrees C. over 10 hours and maintained at about this temperature. The pressure was reduced to 11 mm Hg and volatile material was removed on heating the reactor slowly from 50 to 140 degrees C. The yield of the pure product obtained was 85%.

Step (b): Preparation of ethyl dibromo(dimethylphosphono)acetate

An amount of 186 g of the above ethyl(dimethylphosphonoacetate in 200 ml of $CCL_4$ was added slowly to a slurry of 314.6 g of dibromodimethylhydantoin in $CCl_4$ heated at 50 degrees C. The exothermic reaction maintained the reactor temperature at 60-70 degrees C. without any heating. On completion of the addition, the pale brownish slurry was heated to reflux for 2 hours. The mixture was filtered hot and the filtrate allowed to cool. The dimethylhydantoin which had crystallized out was filtered off and the solvent evaporated in vacuo to give a yield of 100% (on weight basis) of a low melting solid.

The crude material was purified by washing a chloroformic solution with water (3 times with its half volume), the organic phase dried with sodium sulphate and the solvent evaporated in vacuo. The melting point of the product was 43.5–44.5 degrees C. The active Bromine content (determined as described below) was found to be 48.9% (calculated, 45.2%).

The product was also identified by NMR with the following data:

$\delta$=1.38, 3H, t, $J_{HW}$=7.1 Hz; 4.02, 6H, d, $J_{HP}$=10.9 Hz;

4.38, 2H, q, $J_{HW}$=7.1 Hz.

The analyses of the elements were as follows:
P=8.7% (calculated=8.8%).
Br=44.7% (calculated=45.2%).

EXAMPLE 2

Step a: Preparation of dimethyl cyanomethyl phosphonate 2-chloroacetonitrile (100.6 g, 1.33 mole, 1 portion) and trimethyl phosphite (263.8 g, 2.13 mole, 1.6 portion) were reacted as described in Example 1. The product distilled at 94–97.5 degrees centigrade, 0.2–0.25 mm/Hg.

'H n.mr.(200 MHz). $\delta$=3.06, d, 2H, $J_{HP}$=21.1 Hz; 3.88, d, 6H, $J_{HP}$=11.3 Hz. 560 m 705 w 725 w: Refractive Index=1.4331.

Step b: Preparation of dimethyl cyanodibromomethyl phosphonate

The reaction was performed in chloroform according to the procedure of example 1b:

Melting point of the product was 63 to 66 degrees.
Analysis: 'H nm5 (200 MHz)=4.11, d, $J_{HP}$=11.1 Hz.
Elements analysis: N=5.1% (calculated=4.6%) Active $Br_2$=48.7% (calculated=52.1%)

EXAMPLE 3

Preparation of brominated phosphonoacetic acid

Ethyl dimethyl phosphonoacetate as prepared in Example 1 (19.6 g, 0.1 mole) was refluxed with 48% HBr solution (20 ml) for 3 hours. The reflux flask was equipped with a lagged Vigreaux column (2×12 cm) and the reflux rate was adjusted so that the temperature at the head of the column was 85 to 95 degrees C. At the conclusion of the 3 hour period, no more alcohol distilled over. The distillate was collected. The residue was evaporated in vacuo at 100 degrees centigrade and the residual water removed by azeotropic distillation with toluene. The residual toluene was removed by applying a vacuum of 6 mm/Hg at 100 degrees centigrade. A viscous liquid (14.1 g) was obtained which eventually crystallized to a hard white solid (100% weight yield). Melting point 130.5–132 degrees centigrade.

Potentiometric titration: 3 end points, each requiring an equal volume of base. Molecular weight=149 (calculated 140).

Analysis:

P=21.3% (found) (22.1% calculated).

'H nmr (200 MHz) contains about 10% monomethyl ester, on P.

$\delta$=2.78; d, $J_{HP}$=21.5 Hz.
$^{31}$Pnmr (81 NMz) Ref $H_3PO_4$.
$\delta$=26.3; t, $J_{HP}$=21.5 Hz.

This acid could be brominated by halogen transfer using dibromodimethylhydantoin in a manner similar to that of Example 1 (step b).

EXAMPLE 4

Preparation of methyl dibromo(dimethylphosphono)acetate

The reaction was performed according to the procedure of Example 1 (step b) using commercially available methyl dimethylphosphonoacetate.

The elementary analysis of the compound was as follows:

P: 9.2%, compared to 9.1% calculated.
Br: 46.9%, compared to 47.1% calculated.

The NMR spectrum was as follows:

H nmr (200 MHz): o=3.95, s, 3H; 4.03, d, 6H, $J_{HP}$=10.9 Hz.

EXAMPLE 5

Preparation of ethyl dibromo(diethylphosphono)acetate

The reaction was performed according to the procedure of Example 1 (step b) using commercially available ethyl diethylphosphonoacetate. A yellow liquid was obtained in 88% yield (on weight basis).

The active bromine content was found to be 43.1% (compared to the calculated 41.8%).

The elementary analysis of the compound was as follows:

P: 7.8% compared to 8.1% as calculated.
Br: 43.3% compared to 41.9% as calculated.

The NMR spectrum was as follows:

$\delta$=1.33→1.47, m, 9H (1.41, t, 3H, $J_{HH}$=7.0 Hz; 1,40, t, 3H, $J_{HH}$=[7.1H$_3$]

4.25–4.53, m, 6H [q+d o f q].

EXAMPLE 6

Preparation of ethyl dichloro(dimethylphosphono)acetate

Dichlorodimethylhydantoin (9.89 g, 0.05 mole) was slurried in $CCl_4$ (25 ml) and heated to reflux. A solution of ethyl dimethylphosphonoacetate (4.9 g, 0.025 mole) in $CCl_4$ (10 ml) was dropped in over 5 minutes. The suspended solid dissolved. Reflux was maintained for 30 minutes. The mixture was washed with 2 portions of $Na_2CO_3$ (5%) (2×25 ml) and water (2×25 ml). The organic phase was dried over $Na_2SO_4$ and the solvent evaporated in vacuo to give a 90% yield (weight basis) of a pale straw coloured liquid.

Gas chromatographic analysis showed the material to be 95% pure.

Analysis: Total Cl=27.5% (calculated 26.8%) P=12.6% (calculated 11.7%).

Refractive index=1.462.

'H nmr (200 MHz) $\delta$=1.33, t, 3H, $J_{HH}$=7.1 Hz; 3.97, d, 6H, $J_{HP}$=10.8 Hz; 4.35, q, 2H, $J_{HH}$=7.1 Hz.

In the above Examples, the determination of active halogen was performed by iodometry method (described by G. Charlot et al in Quantitative Inorganic Analysis, 1957, page 385).

A sample of material was accurately weighed into a flask containing acetonitrile (5 ml) and $H_2SO_4$ (10%) was added. To the mixture obtained, an excess of potassium iodide (solid form) was added. The liberated iodine was titrated against 0.1N $Na_2S_2O_3$ solution. The titre, in ml/g sample was converted to meq/g by division by 10 and converted to mg Br/g sample using an equivalent weight of 80.

The exact mechanism by which the biocide compositions according to the present invention destroys microorganisms has not yet been established. Several theories, each one having a reasonable basis, can be postulated to explain the biocide activity. It may be that in an aqueous environment, nascent oxygen is liberated which combines with components of cell protoplasm, destroying the organism. Another theory suggests that active halogen combines with proteins of the cell membranes, forming N-halogen compounds which interfere with cell metabolism. Still another theory stipulates that the cell membranes are so altered that diffusion of cell contents outward causes the eventual death of the organism. It is beyond the scope of the present specification to provide additional theoretical aspects as to how the compositions according to the present invention act against the various microorganisms.

The microorganisms (MO's) chosen for testing the biocides were Pseudomonas, Coliforms, Bacillus Megaterium, Enterococcus and Saccharomyces Cerevisiae.

Pseudomonas is a Gram negative, non-sporulating, sturdy MO, naturally present in soil, and considered to be difficult to kill. This is the dominant species in open recirculating cooling systems. Pseudomonas is known to metabolize at leat 75 different organic chemicals, amongst which one can find phenol derivatives and ethane. Chlorine destroys Pseudomonas at concentration less than 0.1 ppm.

Coliforms are Gram negative MO's, which are found in cooling water and especially in swimming pool water, where their count serves as a measure for disinfection efficiency.

Bacillus are Gram positive, spore-forming MO's which may also be found in cooling water. They are nutritionally more demanding than Pseudomonas, and most of them are unable to grow in a medium containing a single organic compound. A few species can ferment sugar if available, but many are obligate aerobes. Spores form only when normal, healthy vegetative cells experience an adverse change in environment. When this occurs, a thick-walled polysaccharide coating surrounds the nucleus within the bacterium producing an endospore. When favorable conditions are re-established the polysaccharide envelope is discarded and the cell again becomes vegetative. Spores can remain viable with negligible respiratory activity for many years. They are killed only with difficulty by chemicals that destroy vegetative cells on contact, because the walls of spores are impentrable to most chemicals except chlorine.

Enterococcus are Gram positive, non-spore-forming MO's, which belong to a long list of microorganisms which may be found in cosmetics.

Saccharomyces cerevisiae is a yeast. Yeast, unlike all the previously mentioned bacteria, contains a true nucleus. Fungi are non-photosynthetic eukaryotes ("possessing a true nucleus"), and divide into several subgroups, one of which are yeasts. Yeasts, unlike other fungi, do not form mycelium. (Mycelium is the interlacing filament growing around the nuclei and cytoplasm, which makes the microorganism a multinucleate mass of continuous cytoplasm.).

The above collection of microorganisms covers, on the one hand, the most abundant bacteria found in water, and on the other hand, it includes representatives of the various types of MO's: Gram negative, Gram positive, non-spore-forming, spore-forming and yeast.

In the following Examples, the phosphorus-based compounds according to the present invention and included in the general formula as given in claim 1, will be illustrated as to their outstanding activity as biocides with various MO's. A series of screening tests were carried out under the same conditions with commercial biocides for comparison purposes with the compounds according to the present invention.

The known biocides which were tested with the results obtained are given in the following Table 1:
1—DBNPA = 2,2-dibromo-3-nitrilopropionamide.
2—Kathon = Mixed 2-methyl-4-isothiazolin-3-ones, produced by Rohm & Haas.
3—MBT = Methylene bis(thiocyanate) produced by Stauffer Chemical Corp.
4—Tektamer: Trade Mark of 1,2-dibromo-2,4-dicyanobutane, produced by Merck & Co. Inc.
5—Bronopol: Trade Mark of 2-bromo-2-nitropropan-1,3-diol, produced by The Boots Co. Ltd.

The compounds according to the present invention used in this test were:
6—Ethyl dibromo(dimethylphosphono) acetate.
7—Dimethylphosphono dibromoacetonitrile.
8—Dimethyl cyanodibromomethylphosphonate.

TABLE 1

Comparison of the Biocidal performance of some bacteriocides. 99.9% kill concentrations* (in ppm).

|  | Bacillus | Saccharomyces Cerevisiae | Pseudomonas | Coliforms | Enterococcus |
|---|---|---|---|---|---|
| 1 - DBNPA | 780 | 700 | 50 | 50 | 100 |
| 2 - Kathon | 210 | 70 | 210 | 160 | 770 |
| 3 - MBT | 1400 | — | 480 | 460 | 1400 |
| 4 - Tektamer | 460 | 880 | 700 | 500 | 1300 |
| 5 - Bronopol | 1050 | 1400 | 1400 | 1400 | 1000 |
| 6 - | 1400 | 1000 | 580 | 100 | 590 |
| 7 - | 1400 | 130 | 100 | 100 | 100 |

*Extrapolated values.

In the following Examples the biocidal efficiency of the compositions according to the present invention will be illustrated in respect to the various microorganisms.

EXAMPLE A

The MIC (Minimum Inhibitory Concentration) in ppm was determined for each of the biocides listed in Table 1, using the standard Pour-Plate technique.

TABLE 2

MIC (in ppm).

| Biocide | Bacillus | Saccharomyces Cerevisiae | Pseudomonas | Coliforms | Enterococcus |
|---|---|---|---|---|---|
| 1 | 1300 | 1200 | 7 | 6 | 500 |
| 2 | 390 | 20 | 2000 | 1740 | 5600 |
| 3 | 1560 | 930 | 2760 | 4680 | 5800 |
| 4 | 1010 | 920 | 2065 | 3420 | 5600 |
| 5 | 2030 | 5000 | 5600 | 4000 | 5800 |
| 6 | 980 | 330 | 150 | 35 | 200 |
| 7 | 203 | 45 | 17 | 25 | 15 |

The overall superiority of Compounds 6 and 7 (according to the present invention) is clearly evident from the data presented in the above Table.

EXAMPLE B

The biocidal efficiency of ethyl(dimethylphosphono)dichlororoacetate was determined vis-a-vis Coliforms and Saccharomyces Cerevisiae as described in the above screening tests. In both cases the concentration required to kill 99.9% of the microorganisms was 50 ppm.

EXAMPLE C

The microbiological activity of the compositions according to the present invention, was tested with liquors obtained from actual streams from the plant of a commercial paper mill. Microorganisms were isolated from such solutions and tested at levels of $10^6$ microorganisms/ml of solution, using 100 ppm of a composition containing equimolar amounts of (dimethylphosphono)-monobromoacetamide (A) and monobromonitrilopropionamide (B). The results obtained are presented in the following Table 3.

TABLE 3

Microbiological activity of a formulation (100 ppm) containing equimolar amounts of (A) and (B) with paper mill liquors.

| Microorganisms (M.O.) isolated from neutral streams (M.O./ml) | | Microorganisms isolated from acid stream (in M.O./ml) | |
|---|---|---|---|
| Initial solution | After 3 hours at pH 7 | Initial solution | After 3h at pH 4 | After 3h at pH 7 |
| $2.5 \times 10^6$ | less than 10 | $1.2 \times 10^6$ | 100 | 50 |

EXAMPLE D

The procedure as in Example B was repeated using instead of the biocide described therein, 100 ppm of an equimolar mixture of $(HO)_2 P(O)CHBrCOOH$ and monobromodimethylhydantoin. These materials are readily dispersed in the aqueous media and reduced the microbiological contamination in both streams to under 100 M.O./ml after 3 hours contact at pH 7.

EXAMPLE E

The activity of compounds 6 and 7 (Table 1) were compared with: 1=(DBNPA) and 2=(Kathon)—both known as excellent biocides —regarding their ability to prevent growth of nitrite oxidising bacteria.

A model cooling tower system, as described in Process Biochem., p. 31 (July/August 1976), was used in these tests. Activity was measured as the reduction of nitrite oxidation capacity (of the bacterial slime) in comparison to a biocide-free system (blank). Residual nitrite in the circulating water was determined by addition of sulfanilic acid and back titration with standard nitrite solution.

The results are given on Table 4.

TABLE 4

Results on the activity to prevent growth of nitrite oxidising bacteria.

| Biocide | Concentration (ppm) | Circulation time (days) | Nitrite concentration (ppm) | Nitrite loss/day (ppm) | Average nitrite loss/day (ppm) |
|---|---|---|---|---|---|
| Control | 0 | 0 | 850 | | |
| | | 3 | 401 | 112 | |
| | | 6 | 150 | 83 | 98 |
| 1(DBNPA) | 150 | 0 | 725 | | |
| | | 3 | 665 | 15 | |
| | | 6 | 623 | 14 | 14.5 |
| 2(Kathon) | 150 | 0 | 693 | | |
| | | 3 | 651 | 11 | |
| | | 6 | 624 | 9 | 10 |
| 6(Table 1) | 150 | 0 | 732 | | |
| | | 3 | 690 | 11 | |
| | | 6 | 671 | 6 | 8.50 |
| 7(Table 1) | 150 | 0 | 682 | | |
| | | 3 | 637 | 11 | |
| | | 6 | 602 | 12 | 11.5 |

We claim:

1. A method of killing or inhibiting the growth of harmful microorganisms selected from the group consisting of gram-negative bacteria, gram-positive bacteria and yeast, which comprises contacting said microorganisms with a biocidal composition comprising an effective biocidal or growth-inhibiting amount of at least one compound having the formula $$(RO)_2P(O)CXYZ$$

wherein R is H, a $C_{1-12}$ aliphatic hydrocarbon radical or a phenyl radical, X is H or halogen, Y is halogen, and Z is CN, with the proviso that X and Y cannot both be Cl.

2. The method according to claim 1, wherein said effective amount is in the range from 0.1 to 5000 parts per million.

3. The method according to claim 1, wherein said compound is dimethyl cyanodibromomethylphosphonate.

4. The method according to claim 1, wherein said biocidal composition further comprises one or more components selected from the group consisting of diluents, extenders and carrier vehicles.

5. A method according to claim 4, wherein said carrier vehicle is water.

6. The method according to claim 1, wherein said biocidal composition further comprises conventional auxiliaries used in aqueous systems selected from the group consisting of corrosion inhibitors, water softeners and masking agents.

7. The method according to claim 1, wherein R is H or $C_{1-12}$ alkyl.

8. A method of killing or inhibiting the growth of harmful microorganisms selected from the group consisting of gram-negative bacteria, gram-positive bacteria and yeast, which comprises contacting said microorganisms with a biocidal composition comprising an effective biocidal or growth-inhibiting amount of diethyl cyanodibromomethyl phosphonate.

* * * * *